United States Patent
Zangiacomi

(10) Patent No.: US 7,138,422 B2
(45) Date of Patent: *Nov. 21, 2006

(54) METHOD FOR CONTROLLING A POPULATION OF SOCIAL INSECTS USING 1-ARYLPYRAZOLES OR 1-HETEROARYLPYRAZOLES

(75) Inventor: Louis Zangiacomi, Dardilly (FR)

(73) Assignee: BASF Agro B.V., Arnhem (NL)-Wädenswil Branch (CH)

( * ) Notice: Subject to any disclaimer, the term of this patent is extended or adjusted under 35 U.S.C. 154(b) by 194 days.

This patent is subject to a terminal disclaimer.

(21) Appl. No.: 10/386,908

(22) Filed: Mar. 12, 2003

(65) Prior Publication Data

US 2003/0228343 A1 Dec. 11, 2003

Related U.S. Application Data

(63) Continuation of application No. 08/981,795, filed as application No. PCT/FR96/00994 on Jun. 26, 1996, now abandoned.

(60) Provisional application No. 60/002,850, filed on Aug. 28, 1995.

(30) Foreign Application Priority Data

Jun. 29, 1995 (FR) .................................. 95 08074
Jan. 29, 1996 (FR) .................................. 96 01238

(51) Int. Cl.
*A01N 43/56* (2006.01)

(52) U.S. Cl. .................. 514/407; 424/405; 424/406; 424/407; 424/408; 424/409; 424/410; 424/84

(58) Field of Classification Search ................ 424/405, 424/406–410, 84; 514/407
See application file for complete search history.

(56) References Cited

U.S. PATENT DOCUMENTS

| 5,232,940 | A | 8/1993 | Hatton et al. ............... 514/407 |
|---|---|---|---|
| 5,306,694 | A | 4/1994 | Phillips et al. ............... 504/253 |
| 5,451,598 | A | 9/1995 | Salmon ....................... 314/404 |
| 5,516,787 | A | 5/1996 | Takada et al. ............... 514/407 |
| 5,547,974 | A | 8/1996 | Hatton et al. ................ 514/406 |
| 5,567,429 | A * | 10/1996 | Senbo ......................... 424/405 |
| 5,928,634 | A * | 7/1999 | Uick et al. ..................... 424/84 |
| 6,517,850 | B1 * | 2/2003 | Gautier et al. .............. 424/405 |

FOREIGN PATENT DOCUMENTS

| AU | 91747/82 | * 12/1982 |
|---|---|---|
| AU | 552549 | 6/1986 |
| EP | 0084310 | 7/1983 |
| EP | 0295117 | 12/1988 |
| EP | 0500209 | 8/1992 |
| FR | 2713889 | 6/1995 |
| FR | 2713891 | 6/1995 |
| WO | 87/03781 | 7/1987 |
| WO | 93/06089 | 4/1993 |
| WO | 94/21606 | 9/1994 |
| WO | 96/16543 A2 | 6/1996 |
| WO | 96/16544 A2 | 6/1996 |
| WO | 96/32014 A1 | 10/1996 |
| WO | 97/11602 A1 | 4/1997 |

OTHER PUBLICATIONS

*Chemical Abstracts*, vol. 123, No. 21, abstract No. 278677 (Nov. 20, 1995).
Mariconi et al, *Sci. Agric.*, vol. 51, No. 3, pp. 505-508 (1994).
DATABASE WPI, Week 8627, abstract No. 86-173308 (1986).
Hamon et al, Proc. Beltwide Cotton Conferences, vol. 2, pp. 759-765, XP000602846 (1996).
DATABASE CROPU, STN-accession No. 96-81812 (1996).
Bloomquist, *Ann. Rev. Entomol.*, vol. 41, pp. 163-190 (1996).

* cited by examiner

*Primary Examiner*—Neil S. Levy
(74) *Attorney, Agent, or Firm*—Hutchison Law Group PLLC

(57) ABSTRACT

A method for controlling a population of social insects such as ants, wasps or cockroaches by administering to a minor fraction of the population an effective amount of a composition that includes a bait and a 1-phenylpyrazole-type compound, particularly 5-amino-3-cyano-1-[2,6-dichloro-4-(trifluoromethyl)phenyl]-4-[(trifluoromethyl)sulphinyl]-1H-pyrazole.

18 Claims, No Drawings

METHOD FOR CONTROLLING A POPULATION OF SOCIAL INSECTS USING 1-ARYLPYRAZOLES OR 1-HETEROARYLPYRAZOLES

CROSS REFERENCE TO RELATED APPLICATION(S)

This application is a continuation application of U.S. patent application Ser. No. 08/981,795, filed on May 27, 1998, now abandoned which was the U.S. national stage of International Application No. PCT/FR96/00994, filed Jun. 26, 1996 and designating the United States, incorporated by reference herein in its entirety and relied upon, which claims the priority of U.S. Provisional Application No. 60/002,850, filed Aug. 28, 1995 (now abandoned), which International Application was published by the International Bureau on Jan. 16, 1997 in French, not in English, as WO 97/01279. This application also claims priority under 35 U.S.C. § 119 to French patent application serial number 95 08074, filed Jun. 29, 1995, and French patent application serial number 96 01238, filed Jan. 29, 1996.

The subject of the present invention is a method for controlling a population of social insects, especially ants, wasps and cockroaches.

It is often very desirable to combat the drawbacks caused by populations of social insects such as ants or wasps or cockroaches, especially in the case of ant populations. Social insects are insects which live in a large society, or in a colony comprising a large number of such insects or congeners.

In the case of ants, for example, these drawbacks generally stem from the inconvenience caused to individuals by the presence or passage of columns of ants in living areas or in the immediate vicinity thereof, such as in the garden or on the patio. The passage of such columns of ants on the lawn next to a private house may especially be particularly unpleasant for the resident wishing to relax by stretching out on the said lawn, on account of the bites inflicted by certain species.

The control of ants is also desirable as regards the cultivation of fruit trees and/or ornamental trees. The reason for this is that certain species of ant provide a role of defending aphids against their predators and thus contribute towards maintaining high populations of aphids, which are harmful to the good health of the trees concerned and/or to fruit yields.

Certain species of ant sometimes cause even greater inconvenience. Thus, the pharaoh ant (*Monomorium pharaonis*) may create anthills even inside living areas, which, in the case of blocks of flats and especially of hospitals, poses hygiene problems.

Now, the inconvenience and/or damage caused by social insects such as ants or wasps or cockroaches, and preferably ants or cockroaches, are in direct proportion with the sometimes very large number which a population of such insects may reach, for example, in the case of ants, the very large number of individuals in the population of an anthill.

Methods for controlling ants or wasps or cockroaches using insecticidal compounds are known. However, these methods are not always satisfactory.

The reason for this is that they often destroy only a small portion of the population concerned, for example, in the case of ants, a fraction of the workers whose function is to collect food outside the anthill. The destruction of this population category is not, however, sufficient to overcome the drawbacks caused by the ants. Indeed, the large capacity of ants to proliferate and their specialization based on the needs of the anthill are capable of rapidly compensating for this destruction, bringing about a new increase in the population.

The known methods moreover have the drawback that it is very difficult to treat all the individuals of the population, especially on account of the fact that, as regards ants, the anthills are fairly inaccessible, since they are generally located at a depth of several tens of centimetres below the surface of the ground.

One aim of the present invention is to overcome these drawbacks.

Another aim of the present invention is to ensure the destruction of the larvae present in the anthill, or more generally in the nest or dwelling place of the said social insects.

Another aim of the present invention is to ensure the destruction of the laying females present in the anthill, or more generally in the nest or dwelling place of the said social insects.

Another aim of the present invention is to propose a method which allows the definitive destruction of all or almost all of a population of social insects such as ants or wasps or cockroaches, preferably such as ants or cockroaches.

It has now been found that these aims could be totally or partly achieved by means of the control method according to the invention which is described in detail below.

The subject of the present invention is thus a method for controlling a population of social insects such as ants or wasps or cockroaches, characterized in that there is applied to a minor fraction of this population an effective amount of a composition comprising a bait and a compound of formula (I):

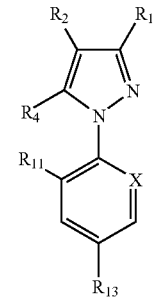

in which:

$R_1$ is a halogen atom or a CN or methyl group;

$R_2$ is $S(O)_n R_3$;

$R_3$ is alkyl or haloalkyl;

$R_4$ represents a hydrogen or halogen atom; or a radical $NR_5R_6$, $S(O)_m R_7$, $C(O)R_7$, or $C(O)O—R_7$, alkyl, haloalkyl or $OR_8$ or a radical $—N=C(R_9)(R_{10})$;

$R_5$ and $R_6$ independently represent a hydrogen atom or an alkyl, haloalkyl, C(O)alkyl or $S(O)_r CF_3$ radical; or $R_5$ and $R_6$ may together form a divalent alkylene radical which may be interrupted by one or two divalent hetero atoms, such as oxygen or sulfur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted with one or more halogen atoms or groups such as OH, —O-alkyl, —S-alkyl, cyano or alkyl;

$R_{11}$ and $R_{12}$ represent, independently of each other, a hydrogen or halogen atom;

$R_{13}$ represents a halogen atom or a haloalkyl, haloalkoxy, $S(O)_qCF_3$ or $SF_5$ group;

m, n, q and r represent, independently of one another, an integer equal to 0, 1 or 2;

X represents a trivalent nitrogen atom or a radical C—$R_{12}$, the other three valences of the carbon atom forming part of the aromatic ring;

with the proviso that when $R_1$ is methyl, then $R_3$ is haloalkyl, $R_4$ is $NH_2$, $R_{11}$ is Cl, $R_{13}$ is $CF_3$ and X is N.

The alkyl radicals in the definition of formula (I) generally comprise from 1 to 6 carbon atoms. The ring formed by the divalent alkylene radical representing $R_5$ and $R_6$, as well as by the nitrogen atom to which $R_5$ and $R_6$ are attached, is generally a 5-, 6- or 7-membered ring.

A preferred class of compounds of formula (I) comprises the compounds where $R_{11}$ is CN and/or $R_3$ is haloalkyl and/or $R_4$ is $NH_2$ and/or $R_{11}$ and $R_{12}$ are, independently of each other, a halogen atom and/or $R_{13}$ is haloalkyl.

Populations of ants are more especially preferred among the populations of social insects which may be controlled using the method according to the invention.

In the sense of the present invention, control of a population of social insects such as ants, wasps or cockroaches is understood to mean the control of the said insects, and more particularly the total or almost total destruction of the said population, in other words the destruction of more than 60%, preferably more than 70% and even more preferably of 95 to 100%, of the said population.

An effective amount of the composition used in the method according to the invention is understood to mean an amount which is capable of controlling the whole population of social insects such as a population of ants or wasps or cockroaches.

More particularly, the invention relates to a method for treating social insects such as ants, cockroaches or wasps with an effective amount of active material of formula (I), this effective amount of composition being an amount used equal to the dose required to destroy at least 90% of the minor fraction of the population of social insects to which the said composition is applied, within a period of between 2 and 30 days, preferably between 2 and 7 days. The minor fraction often corresponds in practice to the population living or circulating outside the common dwelling place or nest.

According to a more preferred variant of the invention, when the population of social insects is a population of ants, the effective amount of composition used for the method according to the invention is generally such that the dose of compound of formula (I) is between 0.05 and 50 mg per anthill treated, preferably from 0.1 to 20 mg. This effective amount may be determined more precisely within this range by systematic tests, depending on the species of ant whose population it is desired to control, and also depending on the size and extent of the anthills which may vary according to the nature of these species.

The invention thus also relates to a method for controlling social insects such as ants, wasps or cockroaches (but preferably cockroaches) which have a common dwelling place or nest in which they live with a substantial population of their congeners, the said method comprising a treatment with an effective dose, preferably a dose of between 0.0001 and 20 grams per 100 m$^2$, of one or more areas frequented by, or assumed to be frequented by, the said social insects (preferably cockroaches), the said area being outside the place of the said common dwelling but being a place in which the cockroaches circulate or are assumed to circulate.

The ants which may be controlled using the method according to the invention are especially:

ants of the genus *Lasius*, for example the black ant (*Lasius niger*);

the pavement ant (*Tetramorium caespitum*);

the pharaoh ant (*Monomorium pharaonis*);

the Argentine ant (*Iridomyrmex humilis*);

fire ants belonging to the genus *Solenopsis*;

fungal ants, such as the ants of the genus *Acromyrmex* (for example the cassava ant) and the ants of the genus *Atta*.

The cockroaches which may be treated by the method of the invention are mainly *Blatella germanica, Blatella orientalis, Periplaneta americana, Periplaneta fuliginosa*.

The compound of formula (I) may be prepared according to one of the methods described in Patent Applications WO 87/3781, 93/6089, 94/21606, and EP 295,117 or alternatively by another method from within the general experience of those skilled in the art competent in chemical synthesis. This compound is also referred to in the remainder of the present text by the term active material.

The bait employed in the composition used in the method according to the invention is a product which is sufficiently appetizing to incite social insects such as ants or wasps or cockroaches to eat it. In the case of ants, this bait is chosen, for example, but not exclusively, from animal and/or plant proteins, or alternatively from fats, also of animal and/or plant origin, or even from mono-, oligo- or polyorganosaccharides, especially from sucrose, lactose, fructose, dextrose, glucose or even molasses or honey.

According to a particularly advantageous variant of the invention, the compound of formula (I) used in the invention is 5-amino-3-cyano-I-[2,6-dichloro-4-(trifluoromethyl)phenyl]-4-[(trifluoromethyl)sulfinyl]-1H-pyrazole.

The minor fraction of the population to which the composition employed in the method according to the invention is applied is generally between 1 and 50% of the total population, preferably between 2 and 20%.

According to a preferred variant of the invention, the population of ants which may be controlled using the method according to the invention is a population of ants living in the same anthill. In this case, the minor fraction of the population to which the composition is applied generally consists of workers whose function is to collect food from outside the anthill, these being known as the harvester workers of the anthill.

According to another preferred variant of the invention, the ant or cockroach population which can be controlled by means of the method according to the invention is a population of cockroaches living in the same common dwelling place for cockroaches.

The dose of compound of formula (I) in the composition used is between 0.0005 and 0.5%, preferably between 0.001 and 0.2%. In the present text, the percentages corresponding to doses are, except where otherwise mentioned, weight/weight percentages.

The dose of bait in the composition used is generally between 1 and 99%, preferably between 30 and 99%. The composition used may also comprise other additives such as a solvent for the active material, a flavoring, a preserving agent, a dye or a bitter agent.

According to a particularly advantageous variant of the method according to the invention, it is preferred to apply the composition by placing it in a closed bait-carrier box containing openings which are reserved, on account of their size, for the exclusive use of ants or cockroaches, or insects of similar size, in an area where these insects are likely to be found. The area may especially be in a public or private place, such as a living area, or alternatively on a balcony, a patio, in a garden or in a field. This variant is of improved safety, since it concerns an active material which is liable to present a risk in the case of accidental contact or ingestion by pets or children.

The invention as described in the present application also applies to termites, but is preferred for ants, cockroaches and wasps.

In the examples which follow the compound of formula (I) used is 5-amino-3-cyano-I-[2,6-dichloro4-(trifluoromethyl)phenyl]-4[(trifluoromethyl)sulfinyl]-1H-pyrazole, referred to as compound A.

EXAMPLE 1

A watch glass containing 10 g of a 0.05% dispersion of compound A in honey is placed 20 cm from the entrance to an active anthill. The ants are of the species *Lasius niger*, for which the fraction of workers whose function is to collect food is in the region of 10% of the total population. The total population is estimated by a count carried out on an untreated anthill, referred to as the control, containing 10,000 individuals.

During the first 2 days, it is observed that the ants head in a column from the anthill to the watch glass, stop to take up the dispersion and then return to the anthill.

After 15 days, no further surface activity is observed around the anthill. An update on the latter is then obtained by excavation.

A destruction rate of greater than 99% is observed.

In particular, all the larvae have been destroyed.

EXAMPLE 2

Tests are carried out on *Blatella Germanica* cockroaches in boxes 36×24×14 cm in size. These boxes comprise a source of water, a shelter consisting of piled pieces of cardboard, and additional food consisting of biscuit pieces. 15 cockroaches are introduced into the box without bait.

After 24 hours, a 2.7 g pellet of bait with 1.35 mg of product of formula (I) is introduced into the box.

After a further 8 hours, the bait and the additional food are removed and 15 new healthy cockroaches are introduced.

64 hours after the introduction of the bait (i.e. 56 hours after removing the bait and introducing new cockroaches), 98.6% of the cockroaches are dead. The level is 100% after 88 hours.

The invention is claimed is:

1. A method for controlling a population of ants, said method comprising applying to a minor fraction of said population an insecticidally effective amount of a composition comprising a bait and the compound 5-amino-3-cyano-1-[2.6-dichloro-4-(trifluoromethyl)phenyl]-4-[(trifluoromethyl)sulfinyl]-1H-pyrazole, said method effecting destruction of more than 60% of said population;

wherein said minor fraction is the portion of the population which lives or circulates outside the common dwelling place or nest and said amount applied is the amount required to destroy at least 90% of said minor fraction in a time of between 2 and 30 days and wherein from 95% to 100% of said population is destroyed.

2. A method for controlling a population of social insects wherein the population of social insects is a population of ants, said method comprising applying to a minor fraction of said population an insecticidally effective amount of a composition comprising a bait and the compound 5-amino-3-1-cyano-l-[2,6-dichloro-4-(trifluoromethyl)phenyl]-4-[(trifluoromethyl)sulfinyl]-1H-pyrazole, said method effecting destruction of more than 60% of said population, wherein said amount applied is the amount required to destroy at least 90% or said minor fraction in a time of between 2 and 30 days wherein said amount applied comprises a dose of between 0.0001 and 20 grams of said compound per 100 $m^2$.

3. A method according to claim 2, wherein said time is between 2 and 7 days.

4. A method for controlling a population of ants, said method comprising applying to a minor fraction of said population an insecticidally effective amount of a composition comprising a bait and the compound 5-amino-3-cyano-1-[2,6-dichloro-4-(trifluoromethyl)phenyl]-4-[(trifluoromethyl)sulfinyl]-1H-pyrazole, said method effecting destruction or more than 60% of said population;

wherein said minor fraction is the portion of the population which lives or circulates outside the common dwelling place or nest and said amount applied is the amount required to destroy at least 90% of said minor fraction in a time of between 2 and 30 days and wherein said amount applied comprises a dose of between 0.0001 and 20 grams of said compound per 100 $m^2$.

5. The method of claim 4, wherein said time is between 2 and 7 days.

6. A method according to claim 4, wherein said minor fraction is between 1 and 40% of the population.

7. A method according to claim 4, wherein said minor fraction is between 2 and 20% of the population.

8. A method according to claim 4, wherein the bait comprises animal protein, plant protein, animal fat, plant fat or mono-, oligo- or polyorganosaccharides.

9. A method according to claim 8, wherein the bait comprises sucrose, lactose, fructose, dextrose or glucose.

10. A method according to claim 8, wherein the bait comprises molasses or honey.

11. A method according to claim 4, wherein the population of ants is a population of ants living in the same anthill.

12. A method according to claim 11, wherein said minor fraction consists of harvester workers from the anthill.

13. A method according to claim 4, wherein the amount of said compound in the composition is between 0.0005 and 0.5%.

14. A method according to claim 4, wherein the amount of said compound in the composition is between 0.001 and 0.2%.

15. A method according to claim 4, wherein the amount of bait in the composition is between 1 and 99%.

16. A method according to claim 4, wherein the amount of bait in the composition is between 30 and 99%.

17. A method according to claim 4, wherein the insecticidally effective amount of said composition is applied by placing it in a closed bait-carrier box having openings which are reserved by size for the exclusive use of ants, in an area in which the minor fraction of the population of ants circulates.

18. A method according to claim 17, wherein said area is a public or private living area, a balcony, a patio, a garden or a field.

* * * * *

UNITED STATES PATENT AND TRADEMARK OFFICE
CERTIFICATE OF CORRECTION

PATENT NO. : 7,138,422 B2  Page 1 of 1
APPLICATION NO. : 10/386908
DATED : November 21, 2006
INVENTOR(S) : Louis Zangiacomi It is certified that error appears in the above-identified patent and that said Letters Patent is hereby corrected as shown below:

IN THE CLAIMS:

Column 5, lines 54-56, "5-amino-3-cyano-1-[2.6-dichloro-4-(trifluoromethyl)phenyl]-4-[trifluoromethyl)sulfinyl]-1H-pyrazole" should read --5-amino-3-cyano-1-[2,6-dichloro-4-(trifluoromethyl)phenyl]-4-[(trifluoromethyl)sulfinyl]-1H-pyrazole--.

Column 6, lines 3-5, "5-amino-3-1-cyano-1-[2,6-dichloro-4-(trifluoromethyl)phenyl]-4-[(trifluoromethyl)sulfinyl]-1H-pyrazole" should read --5-amino-3-cyano-1-[2,6-dichloro-4-(trifluoromethyl)phenyl]-4-[(trifluoromethyl)sulfinyl]-1H-pyrazole--.

Column 6, line 8, "or" should read --of--.

Column 6, line 9, "30 days wherein" should read --30 days and wherein--.

Column 6, line 20, "destruction or more" should read --destruction of more--.

Signed and Sealed this

Twenty-fourth Day of July, 2007

JON W. DUDAS
*Director of the United States Patent and Trademark Office*